United States Patent
Szepetowski et al.

(10) Patent No.: US 11,690,856 B2
(45) Date of Patent: Jul. 4, 2023

(54) COMPOUNDS FOR TREATING CMV RELATED DISEASES

(71) Applicants: INSERM (INSTITUT NATIONAL DE LA SANTE ET DE LA RECHERCHE MEDICALE), Paris (FR); UNIVERSITE D'AIX MARSEILLE, Marseilles (FR)

(72) Inventors: Pierre Szepetowski, Marseilles (FR); Robin Cloarec, Marseilles (FR); Sylvian Bauer, Marseilles (FR); Nadine Bruneau, Marseilles (FR)

(73) Assignees: INSERM (INSTITUT NATIONAL DE LA SANTE ET DE LA RECHERCHE MEDICALE), Paris (FR); UNIVERSITE D'AIX MARSEILLE, Marseilles (FR)

( * ) Notice: Subject to any disclaimer, the term of this patent is extended or adjusted under 35 U.S.C. 154(b) by 359 days.

(21) Appl. No.: 16/758,292

(22) PCT Filed: Oct. 22, 2018

(86) PCT No.: PCT/EP2018/078889
§ 371 (c)(1),
(2) Date: Apr. 22, 2020

(87) PCT Pub. No.: WO2019/081428
PCT Pub. Date: May 2, 2019

(65) Prior Publication Data
US 2020/0338095 A1    Oct. 29, 2020

(30) Foreign Application Priority Data
Oct. 23, 2017    (EP) .................................... 17306455

(51) Int. Cl.
*A61K 31/65* (2006.01)
*A61P 25/28* (2006.01)
*A61K 31/663* (2006.01)

(52) U.S. Cl.
CPC ............ *A61K 31/65* (2013.01); *A61K 31/663* (2013.01); *A61P 25/28* (2018.01)

(58) Field of Classification Search
None
See application file for complete search history.

(56) References Cited

U.S. PATENT DOCUMENTS

| | | | | |
|---|---|---|---|---|
| 4,254,114 A | * | 3/1981 | Triebwasser | A01N 57/20 514/107 |
| 4,330,530 A | * | 5/1982 | Baker | A61K 31/66 424/649 |
| 6,384,081 B2 | * | 5/2002 | Berman | A61K 31/65 514/621 |
| 2002/0013345 A1 | | 1/2002 | Berman | |

OTHER PUBLICATIONS

Tikka et al., "Minocycline, a Tetracycline Derivative, Is Neuroprotective against Excitotoxicity by Inhibiting Activation and Proliferation of Microglia", 2001, The Journal of Neuroscience, 21(8), pp. 2580-2588. (DOI: https://doi.org/10.1523/JNEUROSCI.21-08-02580. 2001) (Year: 2001).*
Cloarec et al., "In Utero Administration of Drugs Targeting Microglia Improves the Neurodevelopmental Outcome Following Cytomegalovirus Infection", Mar. 2018, Frontiers in Cellular Neuroscience, vol. 12, Article 55, pp. 1-15. (doi: 10.3389/fncel.2018. 00055) (Year: 2018).*
Abraham et al: "Minocycline attenuates microglia activation and blocks the long-term epileptogenic effects of early-life seizures", Neurobiology of Disease, vol. 36, No. 2, pp. 425-430, May 1, 2012.
Cloarec et al: "Cytomegalovirus Infection of the Rat Developing Brain in Utero Prominently Targets Immunce Cells and Promotes Early Microglial Activiation", Plos One, vol. 11, No. 7, Jul. 29, 2016.
Dasoky: "Manifestations of symptomatic congenital cytomegalovirus infection and gancyclovir effect", Rawal Medical Journal 2012 Pakistan Medical Association Pak, vol. 37, No. 1, pp. 18-20, 2012.
Ding et al: "Antiviral drug ganciclovir is a potent inhibitor of microglial proliferation and neuroinflammation", The Journal of Experimental Medicine, vol. 211, No. 2, pp. 189-198, Feb. 3, 2014.
Pang et al: "Supressin of glial activation is involved in the protection of IL-10 on maternal *E. coli* induced neonatal white matter injury", Developmental Brain Research, Elsevier Science BV, vol. 157, No. 2, pp. 141-149, Jun. 30, 2005.

* cited by examiner

*Primary Examiner* — My-Chau T. Tran
(74) *Attorney, Agent, or Firm* — WC&F IP (57) ABSTRACT

The present invention relates the field of CMV and CMV related diseases. Using a powerful rat model of CMV infection of the embryonic brain, the inventors have looked for the existence of postnatal neurological and neurosensory manifestations, and have tested whether the early pharmacological targeting of microglia during pregnancy impacts on postnatal phenotypes. Particularly, the inventors tested the clodronate and the doxycycline and showed that these compounds improve the postnatal outcome of the baby. Thus, the invention relates to a compound which modifies the microglia for use in the treatment of CMV related diseases in a subject in need thereof.

12 Claims, 7 Drawing Sheets

COMPOUNDS FOR TREATING CMV RELATED DISEASES

FIELD OF THE INVENTION

The present invention relates to a compound which modifies the microglia for use in the treatment of CMV related diseases in a subject in need thereof.

BACKGROUND OF THE INVENTION

Perinatal and congenital infections cause morbidity and mortality throughout the world. While a large number of pathogens can occasionally be harmful to the unborn child, some are of considerable public health impact, such as *Toxoplasma gondii*, rubella virus, human immunodeficiency virus, zika virus or cytomegalovirus (CMV). CMVs belong to the Herpesviridae family. In human, congenital CMV infection can cause a wide variety of severe neurological diseases and defects (1). Non-exhaustively, these include microcephaly, polymicrogyria, hearing loss, cerebral palsy, epileptic seizures and intellectual disability—notwithstanding the as-yet elusive long-term influence on the emergence of schizophrenia, autism or epilepsy. Despite the incidence and the medical and socioeconomical burden of congenital CMV infections, which overall represent about 1% of all live births, the pathophysiological mechanisms underlying the subsequent neurodevelopmental disorders have long remained elusive (2). In the absence of current effective preventive or curative strategies, understanding the pathogenesis is mandatory before strategies for early interventions can be designed and tested. Pathophysiology is inherently multiple and complicated as it involves different stages, from maternal CMV primary infection or reactivation and the associated maternal immune responses, to infection and dissemination within the embryonic developing brain—not to mention the crossing of the placental and blood-brain barriers.

Insights into the early events that follow CMV infection of the developing brain are particularly needed. There is species-specificity of CMVs and various animal models of CMV infection of the developing brain have been designed, mostly in rodents (3,4). Despite the lack of materno-fetal transmission of CMV infection in rodents, notably because of differences in placental layer organization, and whereas multiple routes (intracranial, intraperitoneal or intraplacental) and developmental timepoints (antenatal or neonatal) of CMV inoculation were used, convergent insights into the alteration and the possible influence of inflammatory and innate and adaptive immune responses have emerged from such models in recent years (5-10). The production of various chemokines and cytokines by glial and microglial cells, the early recruitment of peripheral immune cells of various types, and the altered status of microglia, may all participate in the pathogenesis of congenital CMV infections of the brain. Microglia is targeted by CMV in the human congenital disease (11) and in murine models of intraplacental or neonatal infections (6,12). Recently we reported on a rat model of CMV infection of the developing brain where the prominent infection of brain myelomonocytic cells including microglia by rat CMV, and the early alteration of microglia, were demonstrated (9). Microglial cells originate from erythromyeloid progenitors located in the yolk sac during embryogenesis (13) and represent the resident mononuclear phagocytes of the brain (14,15). They play crucial roles not only in immune defense, maintenance of the neural environment, injury, and repair, but also in neurogenesis, synaptogenesis, synaptic pruning, connectivity, and modulation of synaptic and neuronal activity (16). On the one hand, early microglial response might well combat against CMV infection; on the other hand, it might have detrimental effects by interacting with important neurodevelopmental processes. Hence to which extent and to which direction—favorable or detrimental—early microglia alteration would influence the emergence and severity of such neurodevelopmental phenotypes in the context of CMV infection of the developing brain in utero, represent an important pathophysiological question.

SUMMARY OF THE INVENTION

Using a powerful rat model of CMV infection of the embryonic brain (see reference 9) the inventors have looked for the existence of postnatal neurological and neurosensory manifestations, and have tested whether the early pharmacological targeting of microglia during pregnancy impacts on postnatal phenotypes (see Cloarec R et al, 2018).

Thus, the present invention relates to a compound which modifies the microglia for use in the treatment of CMV related diseases in a subject in need thereof. Particularly, the invention is described by its claims.

DETAILED DESCRIPTION OF THE INVENTION

A first aspect of the invention relates to a compound which modifies the microglia for use in the treatment of CMV related diseases in a subject in need thereof.

In particular, CMV related diseases which could be treated include but are not limited to neurodevelopmental disorders associated with CMV infections or congenital CMV infections, such as retinitis, microcephaly, polymicrogyria, hearing loss, cerebral palsy, epileptic seizures, intellectual disability.

Thus according to the invention, the invention relates to a compound which modifies the microglia for use in the treatment of neurodevelopmental disorders associated with CMV infections or congenital CMV infections, such as retinitis, microcephaly, polymicrogyria, hearing loss, cerebral palsy, epileptic seizures, intellectual disability.

In another embodiment, the compound according to the invention may be useful to treat a baby infected during the pregnancy of his mother or to prevent the transmission of the virus to the baby during the pregnancy or to prevent or treat CMV related diseases in a baby during the pregnancy.

In another particular embodiment, the invention relates to a compound according to the invention for use in the treatment of HCMV infection in a subject in need thereof.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "microglia" denotes a type of glial cells that are located throughout the brain and spinal cord. Microglia account for 10-15% of all cells found within the brain. As the resident macrophage cells, they act as the first and main form of active immune defense in the central nervous system (CNS). Microglia (and other neuroglia including astrocytes) are distributed in large non-overlapping regions throughout the CNS. Microglia are key cells in overall brain maintenance—they are constantly scavenging the CNS for plaques, damaged or unnecessary neurons and synapses, and infectious agents. Since these processes must be efficient to prevent potentially fatal damage, microglia are extremely sensitive to even small pathological changes in the CNS. This sensitivity is achieved in part by the presence of unique potassium channels that respond to even small changes in extracellular potassium. Microglia play crucial roles in the development, the functioning and the pathology of the central nervous system. As a matter of fact microglia is not only involved in immune defense, maintenance of the neural environment, injury, and repair, but also in neurogenesis, synaptogenesis, synaptic pruning, connectivity, and modulation of synaptic and neuronal activity.

As used herein the term "compound which modifies the microglia" denotes a compound which modifies the activity of the microglia or ultimately which depletes or inhibits the microglia. As used herein the term "modifies the activity of the microglia" denotes that the microglia activity is modified with respect to a series of parameters that are used to assess the microglia status and that could consist but are not limited to: the number of phagocytically active microglia cells as determined by immunohistochemistry (IHC) and cell counting with microglia markers such as Iba1 and microglia phagocytic activation markers such as Ed1/Cd68; by qRT-PCR with markers of microglia activated phenotype; by RNA sequencing; by flow cytometry analysis with microglia markers such as CD45, CD11b/c and RT1B; or any other existing and future method to assess microglia reactive status. As used herein the term "a compound which depletes or inhibits the microglia" denotes a compound able to kill (at least partially) the microglia ("depletes"), which is associated with a decrease in the number of microglial cells as assessed e.g. by immunohistochemistry and cell counting., or a compound able to decrease (at least partially) the activation status of microglia ("inhibits"), which is associated with a modification in activation markers as assessed e.g. by immunohistochemistry and cell counting, e.g. by flow cytometry, etc.

In order to test in our experimental conditions the functionality of a putative or already validated inhibitor of microglia or agent which depletes microglia, a test is necessary. For that purpose, an in vivo approach will be favoured because it would better to assess the efficacy of such compound on microglia state in the context of CMV infection of the developing brain. Hence a compound will be challenged for its action on fetal and neonatal microglia by using at least two series of complementary tests: i/IHC and cell counting as described above with Iba1 and Cd68/Ed1 markers; ii/flow cytometry as described above with microglia markers (e.g. CD45, CD11b/c and RT1B).

Thus, the invention also relates to a compound which depletes the microglia for use in the treatment of CMV related diseases in a subject in need thereof.

The invention also relates to a compound which inhibits the microglia for use in the treatment of CMV related diseases in a subject in need thereof.

In a particular embodiment, the compound is a peptide, petptidomimetic, small organic molecule, antibody, aptamers, siRNA or antisense oligonucleotide. The term "peptidomimetic" refers to a small protein-like chain designed to mimic a peptide.

In a particular embodiment, the compound is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity.

In a particular embodiment, the compound is a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da. According to the invention, a compound which modifies the microglia may be selected in the group consisting in clodronate or tetracycline family compound.

As used herein, the tetracycline family compound regroups notably the chlortetracycline, the demeclocycline, the doxycycline, the minocycline, the oxytetracycline, the tetracycline (compound itself) or the tigecycline. Concerning minocycline, this compound has been clearly described as having an effect on microglia, as doxycycline (see for example Tikka T. et al, 2001; Abraham J; et al, 2012 and Yrjanheikki et al, 1998).

In one embodiment, the compound according to the invention is the doxycycline.

Thus, the invention also relates to the clodronate and/or a tetracycline family compound for use in the treatment of CMV related diseases.

The invention also relates to the clodronate and/or a tetracycline family compound for use in the treatment of neurodevelopmental disorders associated with congenital CMV infections in a subject in need thereof.

In a particular embodiment, the compounds which modify (or deplete or inhibit) microglia are used. This type of compound includes but is not limited to: antagonists of colony-stimulating factor 1 receptor (Elmore et al., 2014, Neuron; Rice et al., 2015, J. Neurosci.), ascorbate and other Vitamin C derivatives (Portugal et al., 2017, Sci. Signal.), N-acetyl cysteine-based compounds and other anti-oxidant molecules (Kannan et al., 2012, Sci. Transl. Med.), antagonists of P2Y12 receptors (Eyo et al, 2015, J. Neurosci.), compounds acting on prostaglandins such as salicylates and related analogs or derivatives (Lan et al., 2011, J Neuroinflammation), polyphenols, omega 3 polyunsaturated fatty acids (Vauzour et al., 2015, Neurochem. Int.). Of note, the elusive effect of antiviral compound ganciclovir on microglia proposed previously, has been ruled out since then (see Skripuletz T. et al, 2015).

In another embodiment, the compound which modifies the microglia is a compound genetically-engineered such as siRNAs, miRNAs, shRNAs, or any other nucleic acid based compound. In some embodiments, the compound is a short hairpin RNA (shRNA), a small interfering RNA (siRNA), a microRNA (miRNA) or an antisense oligonucleotide. In a particular embodiment, the compound is siRNA. A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound. Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway whereby the siRNA interferes with the expression of a specific gene. Anti-sense oligonucleotides include anti-sense RNA molecules and anti-sense DNA molecules, would act to directly block the translation of the targeted mRNA by binding thereto and thus preventing protein translation or increasing mRNA degradation, thus decreasing the level of the targeted protein, and thus activity, in a cell. For example, antisense oligonucleotides of at least about 15 bases and complementary to unique regions of the mRNA transcript sequence can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Antisense oligonucleotides, siRNAs, shRNAs of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically mast cells. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

In one embodiment, the compound is a miRNA; as an example, a miRNA which modifies the microglia can be miR-124 (Pomonarev et al., 2011, Nat. Med.; Louw et al., 2016, Nanomedicine: Nanotechnology, Biology and Medicine).

In some embodiments, the compound is an endonuclease. In the last few years, staggering advances in sequencing technologies have provided an unprecedentedly detailed overview of the multiple genetic aberrations in cancer. By considerably expanding the list of new potential oncogenes and tumor suppressor genes, these new data strongly emphasize the need of fast and reliable strategies to characterize the normal and pathological function of these genes and assess their role, in particular as driving factors during oncogenesis. As an alternative to more conventional approaches, such as cDNA overexpression or downregulation by RNA interference, the new technologies provide the means to recreate the actual mutations observed in cancer through direct manipulation of the genome. Indeed, natural and engineered nuclease enzymes have attracted considerable attention in the recent years. The mechanism behind endonuclease-based genome inactivating generally requires a first step of DNA single or double strand break, which can then trigger two distinct cellular mechanisms for DNA repair, which can be exploited for DNA inactivating: the errorprone nonhomologous end-joining (NHEJ) and the high-fidelity homology-directed repair (HDR).

In a particular embodiment, the endonuclease is CRISPR-cas. As used herein, the term "CRISPR-cas" has its general meaning in the art and refers to clustered regularly interspaced short palindromic repeats associated which are the segments of prokaryotic DNA containing short repetitions of base sequences.

In some embodiment, the endonuclease is CRISPR-cas9 which is from Streptococcus pyogenes. The CRISPR/Cas9 system has been described in U.S. Pat. No. 8,697,359 B1 and US 2014/0068797. Originally an adaptive immune system in prokaryotes (Barrangou and Marraffini, 2014), CRISPR has been recently engineered into a new powerful tool for genome editing. It has already been successfully used to target important genes in many cell lines and organisms, including human (Mali et al., 2013, Science, Vol. 339: 823-826), bacteria (Fabre et al., 2014, PLoS Negl. Trop. Dis., Vol. 8:e2671.), zebrafish (Hwang et al., 2013, PLoS One, Vol. 8:e68708.), C. elegans (Hai et al., 2014 Cell Res. doi: 10.1038/cr.2014.11.), bacteria (Fabre et al., 2014, PLoS Negl. Trop. Dis., Vol. 8:e2671.), plants (Mali et al., 2013, Science, Vol. 339: 823-826), Xenopus tropicalis (Guo et al., 2014, Development, Vol. 141: 707-714.), yeast (DiCarlo et al., 2013, Nucleic Acids Res., Vol. 41: 4336-4343.), Drosophila (Gratz et al., 2014 Genetics, doi:10.1534/genetics.113.160713), monkeys (Niu et al., 2014, Cell, Vol. 156: 836-843.), rabbits (Yang et al., 2014, J. Mol. Cell Biol., Vol. 6: 97-99.), pigs (Hai et al., 2014, Cell Res. doi: 10.1038/cr.2014.11.), rats (Ma et al., 2014, Cell Res., Vol. 24: 122-125.) and mice (Mashiko et al., 2014, Dev. Growth Differ. Vol. 56: 122-129.). Several groups have now taken advantage of this method to introduce single point mutations (deletions or insertions) in a particular target gene, via a single gRNA. Using a pair of gRNA-directed Cas9 nucleases instead, it is also possible to induce large deletions or genomic rearrangements, such as inversions or translocations. A recent exciting development is the use of the dCas9 version of the CRISPR/Cas9 system to target protein domains for transcriptional regulation, epigenetic modification, and microscopic visualization of specific genome loci.

In some embodiments, the endonuclease is CRISPR-Cpf1 which is the more recently characterized CRISPR from Provotella and Francisella 1 (Cpf1) in Zetsche et al. ("Cpf1 is a Single RNA-guided Endonuclease of a Class 2 CRISPR-Cas System (2015); Cell; 163, 1-13).

In another embodiment, any of those compounds could be coupled with other compounds such as liposomes, any other type of nanovectors, or other vehicles and engineered so that to improve efficacy and reduce possible side effects, e.g. improve crossing of biological barriers (e.g. placenta, blood-brain barrier) and delivery to the appropriate targets (e.g. fetal brain, microglia).

According to the invention, the term "subject" denotes a mammal, such as a rodent, a feline, a canine, and a primate. Particularly, the subject according to the invention is a human. Particularly, the subject denotes human infected by the CMV. In one embodiment, the subject is a baby. In another embodiment the subject is a new born baby. In another embodiment the subject is a pregnant female. In another embodiment, the subject is a foetus in the womb.

In a particular embodiment, the compound can be administrated orally, intra-nasally, parenterally, intraocularly, intravenously, intramuscularly, intrathecally, intracerebroventricularly, in-utero or subcutaneously to subject in need thereof.

In one embodiment, the compound of the invention is administrated chronically.

As used herein the terms "administering" or "administration" refer to the act of injecting or otherwise physically delivering a substance as it exists outside the body (e.g., a compound which modifies microglia) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

According to the invention, the compound of the invention, may be administrated to the foetus during the pregnancy of the mother, to the mother during her pregnancy and to the baby (new born baby) after the pregnancy.

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A drug typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The invention also relates to a method for treating a HCMV related diseases in a subject in need thereof comprising administering to a subject in need thereof a therapeutically effective amount of a compound which modifies the microglia according to the invention.

Therapeutic Composition

Another object of the invention relates to a therapeutic composition comprising a compound which modifies the microglia for use in the treatment of CMV related diseases in a subject in need thereof.

In a particularly embodiment, the invention relates to a therapeutic composition comprising a compound which modifies the microglia for use in the treatment of neurodevelopmental disorders associated with an CMV infection in a subject in need thereof.

Accordingly, the invention also relates to a therapeutic composition comprising a compound which depleted and/or inhibits the microglia for use in the treatment of CMV related diseases in a subject in need thereof.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular, or subcutaneous administration and the like.

Particularly, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used. Pharmaceutical compositions of the present invention may comprise a further therapeutic active agent. The present invention also relates to a kit comprising an activator according to the invention and a further therapeutic active agent.

For example, anti-HCMV agents may be added to the pharmaceutical composition as described below.

Anti-HCMV agents may be the polymerase inhibitors Ganciclovir, Valganciclovir, Foscarnet or Cidofovir, or other molecules with anti-HCMV potentiel such as artesunate and its derivatives, leflunomide, everolimus, or new anti-HCMV agents such as letermovir or other anti-terminases, and maribavir or other UL97 kinase inhibitors, or amide derivatives of valproic acid. Or any other anti-HCMV compound further developed.

The invention will be further illustrated by the following figures and examples. However, these examples and figures should not be interpreted in any way as limiting the scope of the present invention.

FIGURES

FIG. 1. CMV infection of the embryonic rat brain cause decreased survival and neurodevelopmental defects that can be prevented in utero by microglia-targeted drug-based strategies.

A series of phenotypic investigations was undertaken in the three first postnatal weeks in five groups of rat pups previously subjected to either of the following procedures during pregnancy: vehicle solution injected intraventricularly (icv) at E15 (MEM; n=34 from four litters); CMV icv in pregnant rat fed with doxycycline (DOX) per os all over pregnancy (CMV+DOX; n=36 from four litters); CMV icv in untreated pregnant rat (CMV; n=54 from six litters); CMV with clodronate (CLO) liposomes icv in pregnant rat (CMV+LipoCLO; n=23 from two litters); CMV with phosphate buffer saline (PBS) liposomes icv in pregnant rat (CMV+LipoPBS; n=33 from four litters). Sex ratio did not differ significantly between the five groups at birth (p=0.15, Chi-square test).

(A) Kaplan-Meier survival curves indicated significant decreased survival in the CMV group vs MEM group, and significant rescues in the CMV+DOX and in the CMV+LipoCLO groups vs their untreated counterparts (CMV and CMV+LipoPBS, respectively).

(B) Cumulative body weight (mean±SEM) decreased significantly in the CMV vs the MEM group. Significant improvements were seen in the CMV+DOX and CMV+LipoCLO groups vs their untreated counterparts (CMV and CMV+LipoPBS, respectively).

(C, D) The proportion of animals succeeding to the righting reflex (C) or the cliff aversion reflex (D) sensorimotor tests decreased significantly in the CMV group vs the MEM group, and significantly improved in the CMV+DOX group vs the CMV group, and in the CMV+LipoCLO group vs the CMV+LipoPBS group.

(E) Hindlimb paralysis occurred significantly more frequently in the CMV group vs the MEM group. This improved significantly in the CMV+DOX group (vs the untreated CMV group) and in the CMV+LipoCLO group (vs the untreated CMV+LipoPBS group).

(F) Significant increase in the proportion of pups with generalized tonic-clonic epileptic seizures (GTCS) was observed in the CMV group vs the MEM group. The risk of GTCS significantly decreased with doxycycline (CMV+DOX) and with clodronate liposomes (CMV+LipoCLO) vs their untreated counterparts (CMV and CMV+LipoPBS, respectively).

Note that because of the strong relationship seen between death on the one hand, and the neurological phenotypes on the other hand, a misleading effect of apparent improvement with time could be perceived from curve shapes for conditions without any rescue intervention, as the most severely affected pups were at higher risk of death (e.g. CMV and CMV+LipoPBS cohorts in (C)).

Data were analyzed using univariate Cox analysis (A), mixed model for repeated data (B-D), or Khi2 test with Bonferroni correction (E,F) and results are indicated on the left side of the cohorts legend: *: $p<0.001$; : $p<0.01$; *: $p<0.05$ for all figure panels, except (E) and (F) where *: $p<0.0002$; : $p<0.002$; ns: not significant. Odds ratio (OR) ±confidence intervals are also indicated on the right side of the cohorts legend, and correspond to the risks in the untreated vs their corresponding treated groups, of: postnatal mortality (A); to fail at the test (C,D); of hindlimb paralysis (E); or of GTCS (F). In (E) and (F): ***: $p<0.001$; *: $p<0.05$. NA: not available.

FIG. 2. Clodronate liposomes deplete microglia and reduce CMV spreading in the developing brain.

Recombinant rat CMV allowing expression of GFP (green) in the infected cells, was injected intraventricularly (icv) in embryos from time-pregnant rats at embryonic day 15 (E15). Either of clodronate liposomes (LipoCLO) to deplete microglia, or liposomes with phosphate buffer saline (LipoPBS) used as a control, were co-injected with rat CMV icv.

(A) LipoCLO decreased the number of Iba1$^+$ microglia and of double-labeled Iba1$^+$, Ed1$^+$ phagocytically active microglia. Three to four adjacent coronal brain sections were analyzed by confocal microscopy throughout the entire z-dimension (n=6 brains in each condition). ROI: region of interest (775×775 µm$^2$). Bar: 100 µm. Mann-Whitney test, two-tailed, with Bonferroni correction. **: $p<0.005$.

(B) LipoCLO reduced rat CMV infection of the brain. Brains were analyzed at P1 using fluorescent binocular microscopy. Three sections were selected according to their coordinates in the rostrocaudal axis. CMV infection decreased dramatically after treatment with LipoCLO (n=6 brains in each condition), as quantified by measuring the proportion of fluorescent (GFP) areas. Bar: 1 mm. Mann-Whitney test, two-tailed. ***: $p<0.001$.

FIG. 3. CMV infection of the embryonic rat brain leads to altered microglia phenotype which is rescued by maternal feeding with doxycycline throughout pregnancy.

(A) Microglia status in the lateral ventricles was assessed on coronal sections observed by confocal microscopy at P1 by quantifying microglial cells (Iba1$^+$) and phagocytically active microglial cells (Iba1$^+$, Cd68/Ed1$^+$). Those values were then used to calculate the phagocytic activation index (PAI) defined as the ratio of the number of Iba1$^+$, Ed1$^+$ activated cells to the total number of Iba1$^+$ cells. PAI increased in the CMV vs the MEM group. Doxycycline (CMV+DOX) significantly counteracted PAI increase (n=6 brains in each condition). ROI: region of interest (387×200 µm$^2$). Bar: 50 µm. Kruskall-Wallis test followed by Dunn's post-hoc test. *: $p<0.05$.

(B,C) Flow cytometry analysis of leukocytes collected at P1 (B) and P7 (C). Total leukocytes (CD45 events) were gated for CD45 and Cd11b/c, thus defining fractions I (lymphocytic cells), II (myelo-monocytic cells) and III (resident microglial cells). Fraction III corresponding to $CD45^{low/int}$, $CD11b/c^+$ microglial cells was further characterized for RT1B expression to identify reactive microglia ($RT1B^+$; fraction IV). Representative flow cytometry plots and the corresponding quantifications are shown for each group. (B) At P1, the increased proportion of reactive microglia triggered by CMV infection was significantly counteracted by doxycycline (n=6 MEM; n=11 CMV; n=12 CMV+DOX). (C) At P7, i.e. seven days after discontinuation of doxycycline, the decreased proportion of total microglial cells (fraction III) and, within that fraction, the increased proportion of reactive microglia (fraction IV) triggered by CMV infection, were not counteracted by doxycycline treatment given in utero (n=6 MEM; n=12 CMV; n=12 CMV+DOX).

Kruskall Wallis test followed by Dunn's post test. *: p<0.001; : p<0.01; *: p<0.05; ns: not significant.

FIG. 4. Maternal feeding with doxycycline throughout pregnancy does not impact on rat CMV infection of the brain.

Green fluorescent protein (GFP) expression was used to monitor infection of the pups' brains by rat CMV with two independent methods.

(A) qRT-PCR. Relative mRNA expression of GFP was assessed by quantitative RT-PCR in CMV-infected brains at P1, using RPL-19 as reference gene. No difference was found between the CMV+DOX group (n=14) and its untreated counterpart (CMV; n=18). Values of fold change represent averages from triplicate measurements for each sample. Mann Whitney test, two-tailed. ns: not significant.

(B) Flow cytometry. Relative proportion of $GFP^+$, CMV-infected cells was estimated by flow cytometry analysis of $CD45^+$ cells isolated from CMV-infected brains at P1 and at P7. No difference was found between the CMV+DOX group (n=12) and its untreated counterpart (CMV; n=11). Mann Whitney test, two-tailed. ns: not significant.

EXAMPLE

Material & Methods
Ethical Statement

Animal experimentations were performed in accordance with the French legislation and in compliance with the European Communities Council Directives (2010/63/UE). Depending on the age of the animals, euthanasia were performed after anesthesia with 4% isoflurane with overdose of pentobarbital (120 mg/kg) or with decapitation. This study was approved under the French department of agriculture and the local veterinary authorities by the Animal Experimentation Ethics Committee (Comité d'Ethique en Expérimentation Animale) no 14 under licences no 01010.02 and no 2016100715494790.

CMV Infection and Pharmacological Treatments

Wistar rats (Janvier Labs, France) were raised and mated at INMED Post Genomic Platform (PPGI) animal facility. Rat cytomegalovirus (rat CMV) recombinant Maastricht strain (RCMV-Δ145-147-gfp) with a green fluorescent protein (GFP) expression cassette, and its production, purification and titration, were reported previously (17). In utero icv injections were performed at E15 as previously described (9,18) in embryos from timed pregnant rats that were anaesthetized with ketamine (100 mg/kg)/xylazine (10 mg/kg). Microglia was depleted in vivo with clodronate liposomes icv (0.5 μL/injection, Encapsula Nanosciences) co-injected with 1.75 $10^3$ pfu of rat CMV; alternatively, phosphate buffer saline (PBS)-containing liposomes (0.5 μL/injection) were co-injected as a control (untreated condition). Microglia status was modified in the embryos in vivo with doxycycline per os given to the mother throughout pregnancy (200 mg/kg in food pellet chow, Bioserv).

Immunohistochemistry Experiments

Immunohistochemistry experiments were carried out on coronal brain slices (50-100 μm, vibratome, Microm; 14 μm, cryostat, Leica) as described previously (9) with the following primary (anti-Iba1: 1/500, Wako; anti-Cd68, Ed1 clone: 1/200, Millipore) and secondary (Alexa Fluor 568 or 647-conjugated goat anti-rabbit or anti-mouse IgGs; Life Technologies) antibodies. Hoescht 33258 (1:2000, Sigma) was used for nuclei staining.

Quantitative Reverse Transcription Polymerase Chain Reaction (qRT-PCR)

Total RNAs were extracted from whole CMV-infected brains at P1 using TRIZOL reagent (Life Technology). cDNA was synthesized from 1 μg of total RNA using Quantitect Reverse Transcription Kit and according to manufacturer protocol (Qiagen). RT-PCRs were then carried out using SYBR-Green chemistry (Roche Diagnostics) and Roche amplification technology (Light Cycler 480). PCR primers were designed for GFP transcripts (forward: 5'-gggcacaagctggagtaca; reverse: 5'-cttgatgccgttcttctgc) and for control gene Rpl19 (ribosomal protein L19) (9). Primer pairs were optimized to ensure specific amplification of the PCR product and the absence of any primer dimer. Quantitative PCR standard curves were set up for all.

Microscopy, Cell Counting and Image Analyses

Images of brain slices were acquired with a Stereo Microscope Olympus SZX16 equipped with digital camera DP73, or a Zeiss Axio Imager Z2 microscope with structured illumination (ApoTome) equipped with Zeiss AxioCam MRm camera and processed using Axiovision software, or with a confocal laser scanning microscope Leica TCS SP5X equipped with a white light laser, a 405 nm diode for ultra-violet excitation, and 2 HyD detectors.

For cell counting analyses, at least three adjacent brain sections were analyzed throughout the entire z-dimension for each sample using confocal microscopy. Images were acquired (1024×1024 pixels) using the 40× oil-immersion objective (NA 1.30) and were composed of three channels corresponding to GFP (488 nm), Iba1 (568 nm) and ED1 (633 nm). Cells were counted manually in each brain with Cell Profiler cell image analysis software (Broad Institute Cambridge, Mass., USA). For each channel of stack images, mean image intensity was measured using "MeasureImage-Intensity" module and cells were identified with "Identify-PrimaryObjects" module, in which Min and Max typical diameter of objects was set between 20 and 80 pixel units, respectively, and threshold was corrected by the mean intensity measured previously. Then, using mask images generated with the aforementioned module, colocalization between channels was evaluated with "RelateObjects" and "MaskObjects" in order to determine the number of overlapping objects. Finally, data were exported to a spreadsheet containing the number of quantified cells for each staining and of colocalizations. This pipeline was validated on sample images before applying it to the whole set of experimental pictures. Fluorescence quantification of the infected brain areas in coronal brain sections selected according to their coordinates as indicated in the rat brain atlas reference (19) and excluding the meninges, was done using ImageJ software. Phagocytic activation index (PAI) of microglia in a given region of interest (ROI) was defined as the ratio of the number of Iba1+ Ed1+ cells to the total number of Iba1+ cells.

Flow Cytometry

Leukocytes from brains obtained from anesthetized P1 or P7 pups were isolated as previously described (9). 1 to $3 \times 10^6$ leukocytes were incubated with Zombie NIR Fixable Viability kit (1:200; Bio legend) for 20 min at RT. Fc receptors were blocked using mouse anti-rat CD32 antibody (FcγII receptor, clone D34-485) for 10 min. at 4° C. to prevent against nonspecific binding. Cells were then stained with antibodies against combinations of cell surface markers as previously listed and described (9). An average of $1.3 \times 10^5$ living singlet cells were analyzed per brain equivalent on a BD LSRFortessa cell cytometer and raw data were analyzed using FACSDiva V8.0 software (BD Biosciences).

Phenotyping

Acquisition of classical developmental reflexes (righting reflex and cliff aversion reflex) was monitored daily between P1 and P16 (for clodronate liposomes rescue experiments) or P20 (for doxycycline rescue experiments). For righting reflex evaluation, rat pups were placed in a supine position, and the time required to flip to the prone position was measured. For the cliff aversion reflex, animals were placed with their forepaws overhanging the edge of a board; the time required to turn >90° away from the edge was recorded. For both tests, a maximum observation time of 30 sec. was used; in case the pup did not succeed in performing the test within the allotted time, the maximal time of 30 sec. was assigned. The presence of hindlimb paralysis was determined visually in animals that had a postural misplacement and immobility of their hindlimbs. Generalized tonic-clonic epileptic seizures were detected visually, usually after animal handling, especially during cage changing and behavioral testing. They consisted in a classical behavioral sequence including (i) movement arrest and loss of postural equilibrium (ii) hypertonic posture of the trunk, limbs and tail, symmetrically, and (iii) repeated, large clonic movements of all limbs, often with respiratory arrest, incontinence, motor automatisms such as chewing and grooming, terminated by a catatonic phase. For auditory experiments, four needle electrodes were placed subcutaneously under 1.5% isoflurane anesthesia. For each rat, the reference electrode was inserted beneath the pinna of the assessed ear, the positive electrode beneath the skin on the vertex of the head, the ground electrode on the animal's back. Evoked potentials were performed using the Echodia® (Saint-Beauzire, France) apparatus and the RTlab software. Headphones with appropriate earplugs were used as acoustic transducers. Clicks, 12 kHz and 24 kHz tone bursts were delivered at a frequency of 17 Hz. Filters were set at 150-1500 Hz. Rejection threshold was defined at 20 µV. Impedances were monitored to be below 2000Ω. Responses for 250 sweeps were averaged at each intensity level. The stimulus intensity was decreased by 10 dB steps sound pressure level (SPL) alternating right and left ears. A contralateral auditory masking was used for high intensity stimulations (>45 dB). Thresholds were defined as the lowest level at which a reproducible wave IV response could be obtained; the curves were analyzed by two different researchers, of whom one was blinded to the study. Profound hearing loss and cophosis were defined by the absence of reproducible wave IV at 90 dB (at 80 dB for the 12 kHz tone bursts); if no threshold was identified at 90 dB, the recording was repeated on the following day to exclude any technical problem. For statistics' sake, these thresholds were set at 100 dB.

Statistics

Data were expressed as means ±s.e.m. unless otherwise stated. Non-parametric Mann Whitney test (two-tailed) followed by Bonferroni correction if needed, and non-parametric Kruskall-Wallis test to detect heterogeneous distribution between groups followed by Dunn's post test for multiple comparisons. were used whenever appropriate. Univariate Cox analysis and Fisher's exact test (two-tailed) were used to compare between survival distributions and rates and parametric Student's t test was used to compare between weight gains, whereas Chi-square test with Bonferroni correction and mixed model for repeated data using PROC GLIMMIX with sas 9.4 were used for all other phenotypic comparisons between groups of animals.

Results

CMV Infection of the Rat Fetal Brain Leads to Postnatal Mortality and to Neurological Manifestations To see whether CMV infection and the accompanying immune responses in the developing rat brain could be associated with the emergence of postnatal consequences recalling those seen in the corresponding human congenital disorder, recombinant rat CMV expressing green fluorescent protein (GFP) was injected intraventricularly (icv) in embryos from timed-pregnant rats (embryonic day 15, E15) as previously described (9).

Figure 1A:
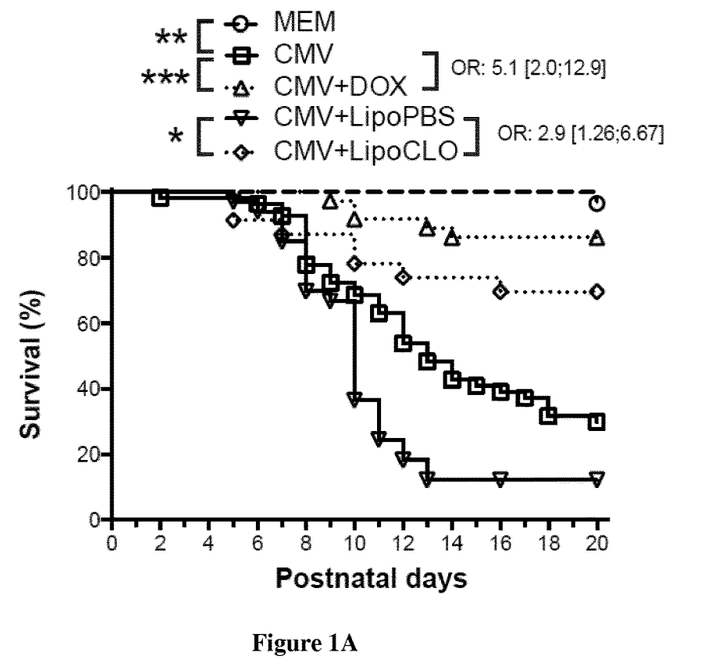
Figure 1B:
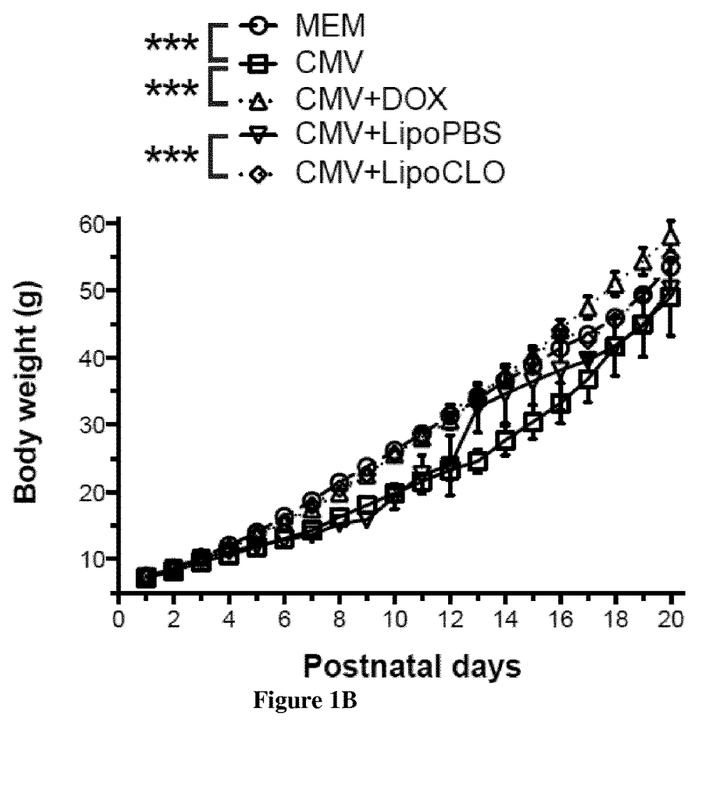

During the period of evaluation, i.e. until postnatal day 20 (P20), CMV infection significantly decreased postnatal survival as compared with control animals who were injected icv with the vehicle (MEM) (p=0.0017) (FIG. 1A). Indeed, 70.4% (38 out of 54 pups) of CMV-infected newborns died in the first three postnatal weeks, compared to 2.9% (one out of 34) controls ($p<10^{-4}$, Chi2 test). In contrast, antenatal mortality was not affected: no significant difference was observed in the ratio of live animals at birth (72.8%, n=103) as compared to the control situation (68.5%, n=54) (Fisher's exact test, two-tailed). Body weight was similar at P1 between CMV-infected (7.20 g±0.10) and control (7.40 g±0.11) newborns (Student's t test), but CMV infection in utero significantly impacted on the postnatal evolution of body weight gain ($p<10^{-4}$) (FIG. 1B).

Congenital CMV infection is the leading cause of non-hereditary congenital sensorineural hearing loss (20). Auditory tests were performed at P40. Hearing thresholds were significantly higher for clicks (p=0.0146) and for 24 kHz bursts (p=0.0017) in the CMV group than in the control group (data not shown). As hearing loss caused by congenital CMV infection may be progressive in children, we aimed at evaluating hearing thresholds in CMV-infected animals at later ages. However, a significant deterioration of hearing thresholds was detected in MEM-injected rats between P40 and P60 (data not shown); this restrained us from performing such a longitudinal analysis in CMV-infected rats as the deterioration seen in controls would likely preclude reliable interpretation of the overall data.

Figure 1C:
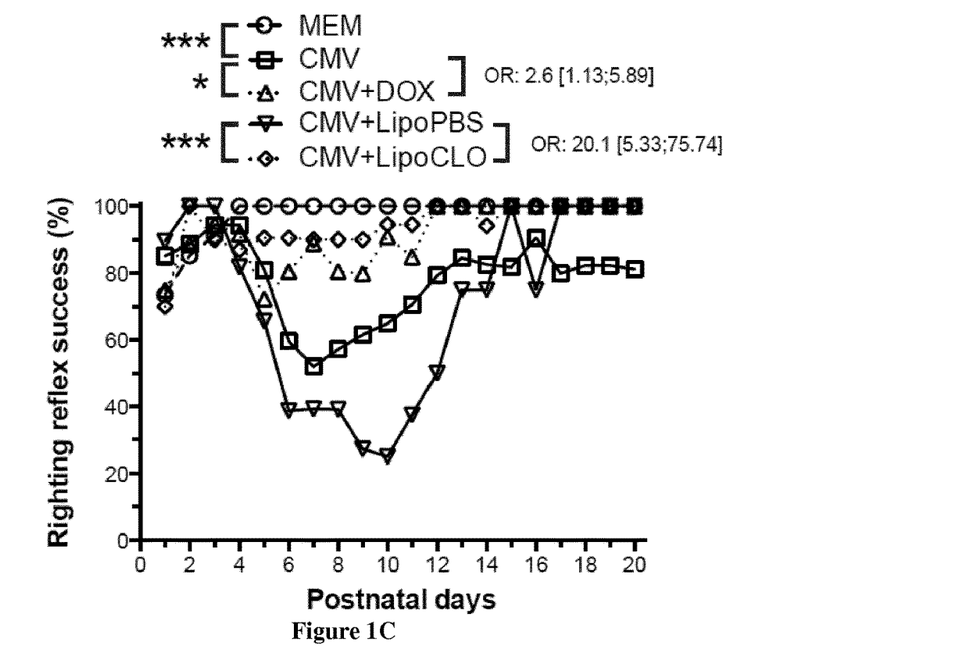
Figure 1D:
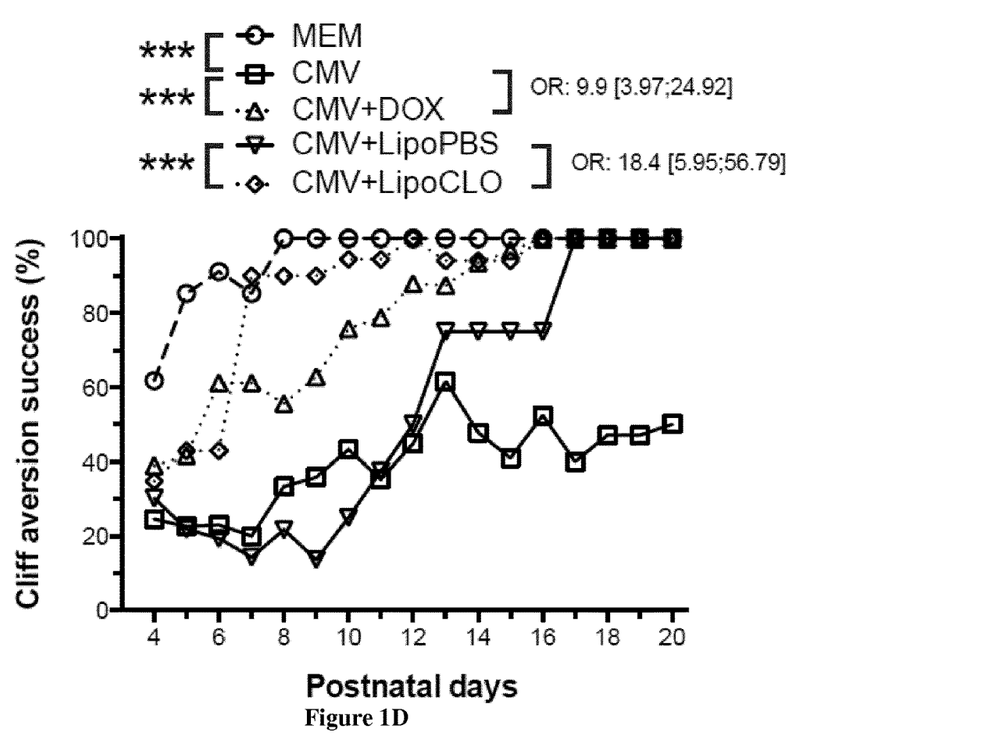
Figure 1E:
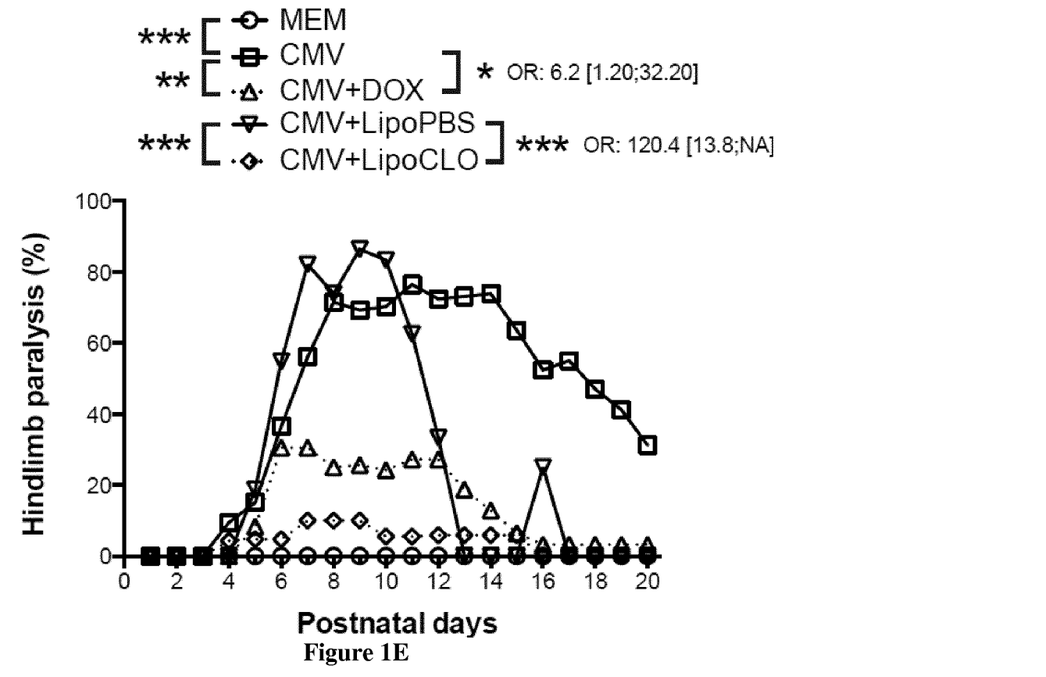

Human congenital CMV infection is also well known to be a contributing cause of cerebral palsy, a group of disorders involving variable degree of sensorimotor disabilities (21). Sensorimotor development was evaluated by daily monitoring pups between P1 and P20 for the acquisition of the classic righting and cliff aversion reflexes (22). The righting reflex consisted in assessing the ability of rodent pups to coordinate the necessary movement to roll over from their backs onto their paws. A significant proportion of CMV-infected pups showed inability to right, as compared with MEM-injected pups who all performed the test successfully ($p<10^{-4}$; FIG. 1C). In the cliff aversion test, pups were placed with their forepaws overhanging the edge of a board and the time required to turn away from the edge was recorded. Control MEM-injected rats showed a clear performance improvement as from P4, and all succeeded to the test after P8 (FIG. 1D). In contrast, a significant proportion of CMV-infected pups was unable to complete the cliff aversion test all along the first three postnatal weeks ($p<10^{-4}$; FIG. 1D). Hindlimb paralysis was detected in the first three postnatal weeks in 83.3% of CMV-infected pups, likely preventing animals from turning away from the cliff, but was not seen in any non-infected pup ($p<10^{-4}$; FIG. 1E).

Figure 1F:
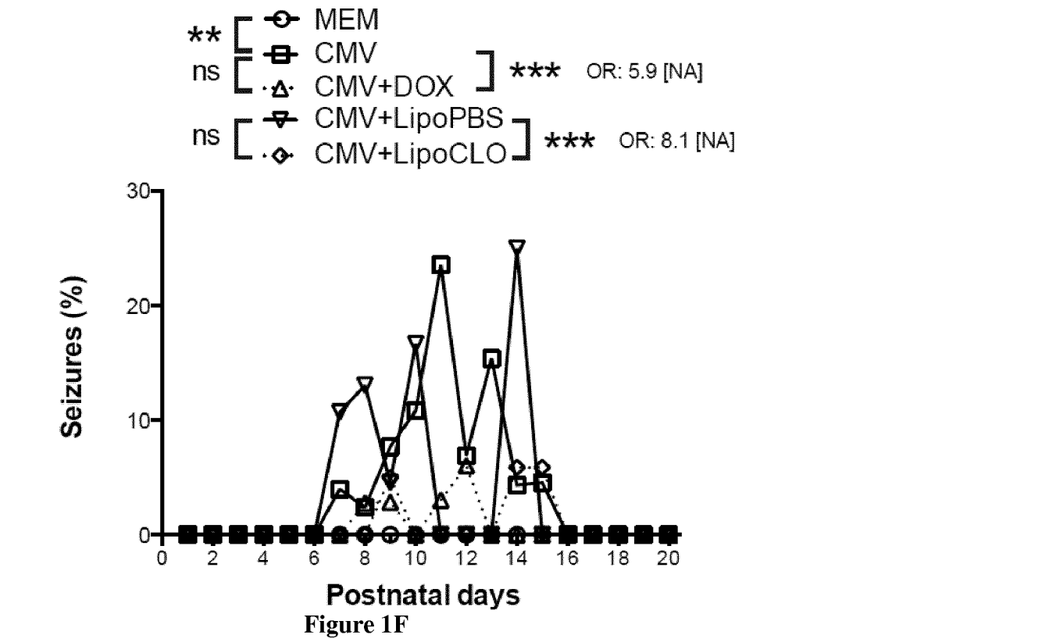

Patients with human congenital CMV are also at high risk of postnatal epileptic seizures (23). Consistently, 24.1% of CMV-infected rat pups exhibited generalized tonic-clonic seizures (GTCS) at least once in the first three postnatal weeks whereas none of MEM-injected pups ever showed any GTCS (p=0.002; FIG. 1F). Interestingly, there was a clear relationship between epilepsy and death: 85% of epileptic rats deceased, as compared to 37% of nonepileptic rats ($p<10^{-4}$, Chi2 test). Similarly, 72% of rats with hindlimb paralysis deceased during the period of evaluation, as compared to 13% of nonparalyzed rats ($p<10^{-4}$).

Acute icv Injection of Clodronate Liposomes In Utero Depletes Microglia and Improves the Postnatal Outcome The consequences of rat CMV infection as described above, recapitulated several cardinal clinical features of the human pathology. The early and prominent infection and alteration of microglia upon CMV infection of the developing rat brain in utero (9) suggested that microglia might be important players in the pathophysiology of congenital CMV. In order to evaluate the possible impact of microglia on the emergence of the neurological and other developmental defects, experiments were designed to target microglia with drugs during pregnancy.

Figure 2A:
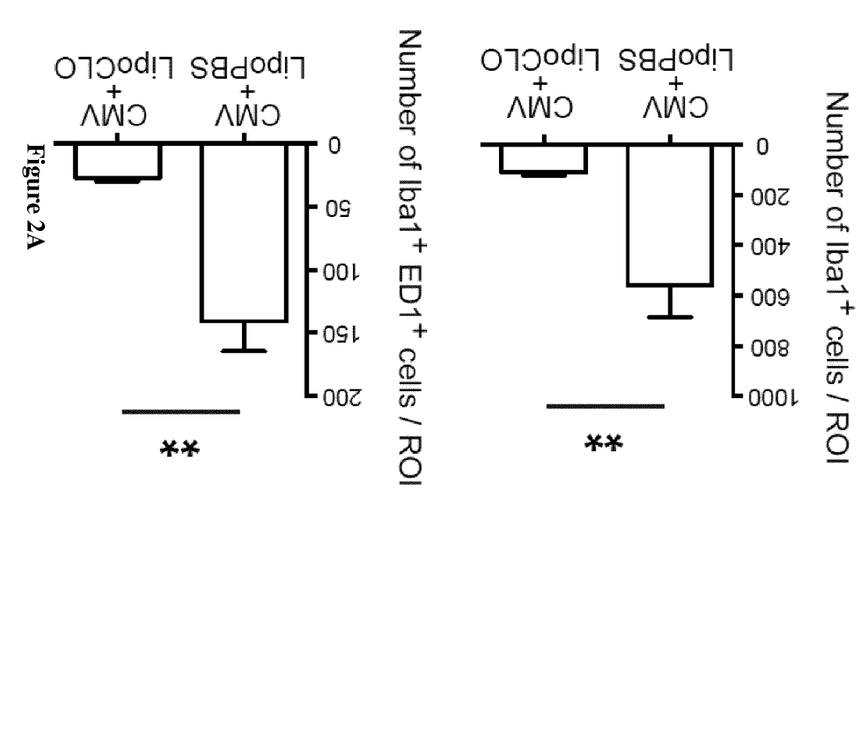
Figure 2B:
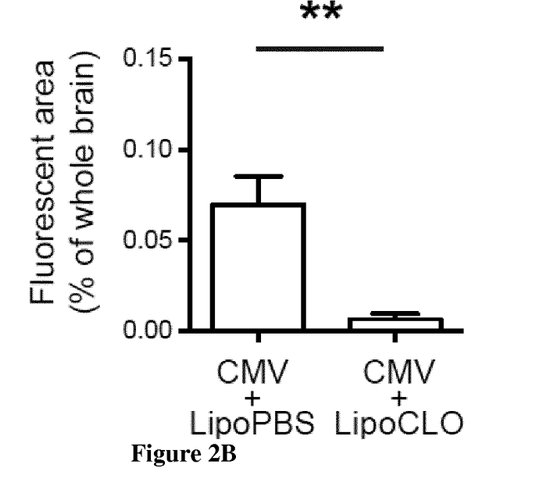

In a first series of experiments, microglia were acutely depleted with clodronate liposomes co-injected icv together with rat CMV at E15. Under such a treatment, brain phagocytes recognize the liposomes as foreign particles and engulf them. Following fusion of phagosomes with lysosomes, clodronate is released into the cytosol and a non-hydrolysable ATP analog is produced, ultimately leading to cell death. Immunohistochemistry experiments confirmed that clodronate liposomes triggered a significant decrease in the total number of Iba1$^+$ microglial cells in the lateral ventricular area taken as the region of interest (ROI) at P1 (112.3 cells/ROI±9.37), as compared to the condition where PBS liposomes were used (558.5 cells/ROI±128.3; p=0.0022; FIG. 2A). A significant decrease in the absolute number of phagocytically active, Iba1$^+$ Ed1(CD68)$^+$ microglia was also oberved (clodronate liposomes: 27.17 cells/ROI±2.80; PBS liposomes: 141 cells/ROI±23.82) (p=0.0022). This was associated with a dramatic reduction of CMV spreading, as GFP$^+$ infected cells were barely visible within the brains of treated embryos. This was confirmed by quantifying the percentage of fluorescent areas in coronal brain sections taken from treated and untreated pups at P1 (p=0.0022; FIG. 2B).

Microglia depletion and reduction of brain CMV infection were associated with a significant improvement of survival and neurodevelopmental outcomes. Postnatal mortality was reduced by 2.9 fold (p=0.012) in clodronate-treated, CMV-infected pups, as compared with untreated, infected pups (FIG. 1A). Indeed, 69.6% (16 out of 23 newborns) of clodronate-treated, CMV-infected newborns had survived at P16, as compared to 12.1% (4 out of 33) of untreated, CMV-infected newborns ($p<10^{-4}$, Chi2 test). Similarly, a significant increase in body weight gain was observed ($p<10^{-4}$; FIG. 1B).

CMV-infected pups treated with clodronate liposomes in utero also performed significantly better at the righting and the cliff aversion reflexes when compared to infected pups who had received control (PBS) liposomes in utero (FIG. 1C, 1D). With clodronate the odds in favor of success to righting and to cliff aversion were at 20.1:1 and 18.4:1, respectively ($p<10^{-4}$ for both). Hindlimb paralysis also improved significantly ($p<10^{-4}$) with clodronate liposomes (17% of rat pups) as compared with control liposomes (88%) (FIG. 1E); there was a dramatic, 120.4 fold decrease in the risk to hindlimb paralysis in clodronate-treated CMV-infected rats ($p<10^{-4}$). Epileptic seizures also occurred less frequently in the first three weeks of life upon treatment with clodronate liposomes (8.7% of rats experiencing at least one seizure), as compared to PBS liposomes (24.2% of epileptic rats) but this difference did not reach statistical significance (p=0.14) (FIG. 1F); however when the risk of seizures was considered, it decreased significantly by 8.1 fold in clodronate-treated, CMV-infected rats when compared to their PBS-liposomes counterparts ($p<10^{-4}$).

Hence a single injection of clodronate liposomes at the time of CMV icv infection not only led to depletion of microglia and to a dramatic reduction of active CMV infection in the rat developing brain, but also to a stuning improvement of survival, body weight gain, sensorimotor development and epileptic seizures in early postnatal life.

Chronic Administration of Doxycycline to Pregnant Mothers Improves Microglia Phenotype In order to confirm the possible role of microglia in the emergence of phenotypes associated with brain CMV infection, as suggested by the microglia depletion experiments described above, an independent series of experiments was designed. Tetracyclines can efficiently modify microglia status in the brains of rat pups after chronic maternal administration during pregnancy (24). Tetracyclines impact on microglia phenotype independently of their canonical antibacterial action (25). Doxycycline, a second-generation, lipophilic tetracycline that crosses blood-brain and placental barriers, was administrated per os to pregnant dams from E0 to birth and its effect on microglia phenotype was tested by immunohistochemistry in the lateral venticular area, a region where active CMV infection was frequently detected (9), and by multicolor flow cytometry analysis of the whole brain.

Figure 3A:
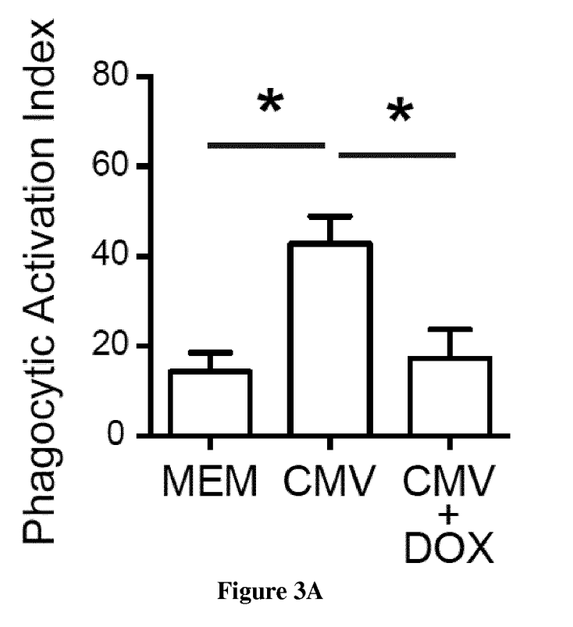
Figure 3B:
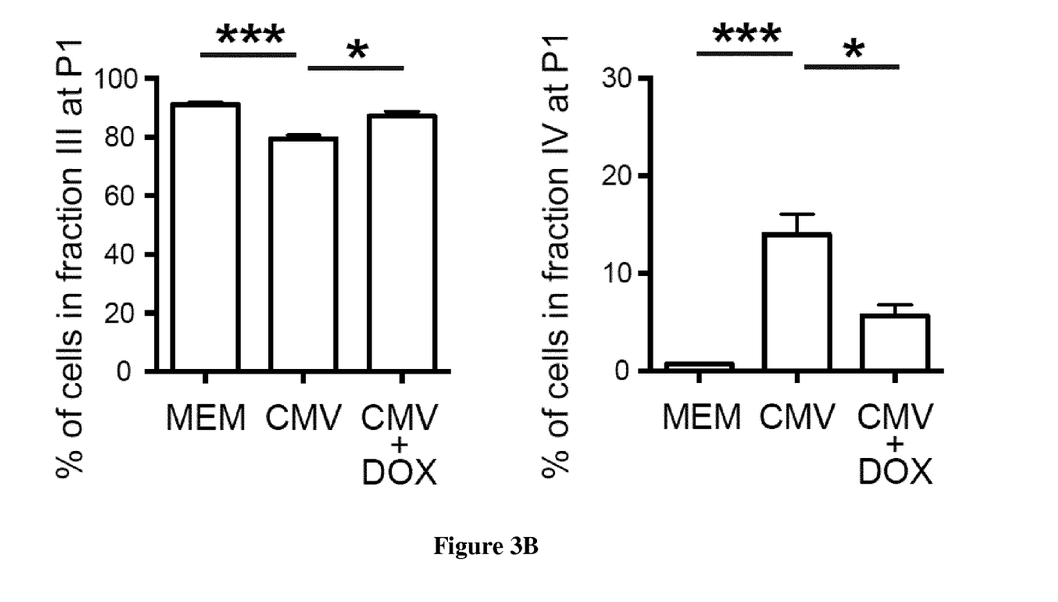
Figure 3C:
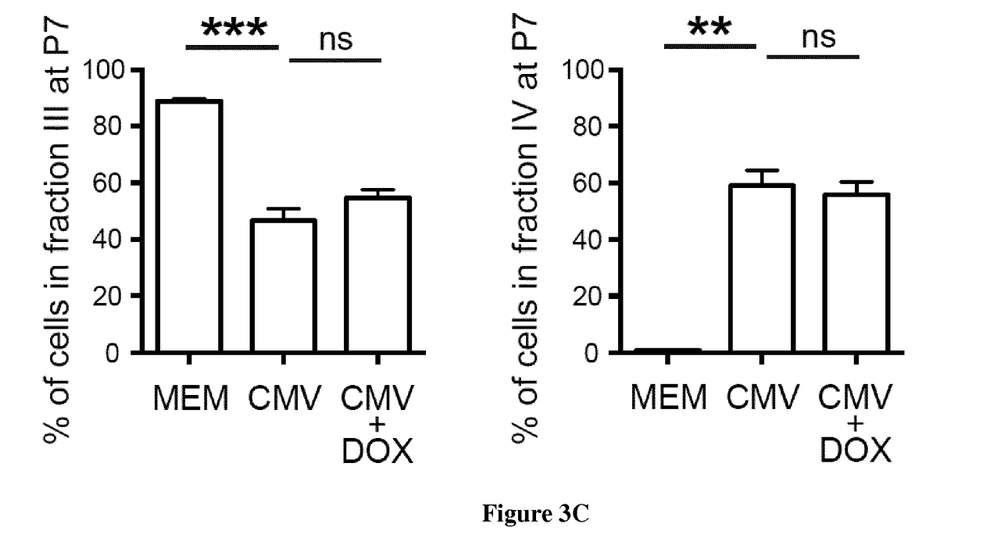

In line with previously reported experiments (9), rat CMV infection at E15 led to a significant increase in the proportion of phagocytically active, Iba1$^+$ Ed1(CD68)$^+$ microglia/macrophages cells at P1. Indeed, the phagocytic activation index (PAI), defined as the ratio of Iba1$^+$ Ed1$^+$ cells to the total number of Iba1$^+$ cells, was significantly increased (42.74%±6.16) as compared with control (MEM-injected) rats (PAI=14.28%±4.29) (p=0.0174), and was significantly improved by doxycycline (17.32%±6.44; p=0.0321) (FIG. 3A). Consistent data were obtained when whole brains were analyzed at P1 by flow cytometry (FIG. 3B). As previously reported (9), a significant increase in the proportion of major histocompatibility (MHC) class II-positive microglia (fraction IV: $CD45^{low/int}$, CD11b/c$^+$, RT1B$^+$) was detected in CMV-infected brains (13.98%±2.12) as compared with controls (0.73%±0.05; p<0.0001); this increase was significantly counteracted in doxycycline-treated, CMV-infected pups (5.66%±1.13) (p=0.0483). The proportions of other types of CD45$^+$ hematopoietic cells were not changed by doxycycline (FIG. 3B). Importantly, the favorable impact of the doxycycline in utero treatment on reactive microglia seen at P1 did not last after treatment discontinuation: at P7, the proportions of reactive, $CD45^{low/int}$, CD11b/c$^+$, RT1B$^+$ microglia (fraction IV) were similar in treated (55.76%±4.60) and in untreated (58.93%±5.54) CMV-infected rats.

Figure 4A:
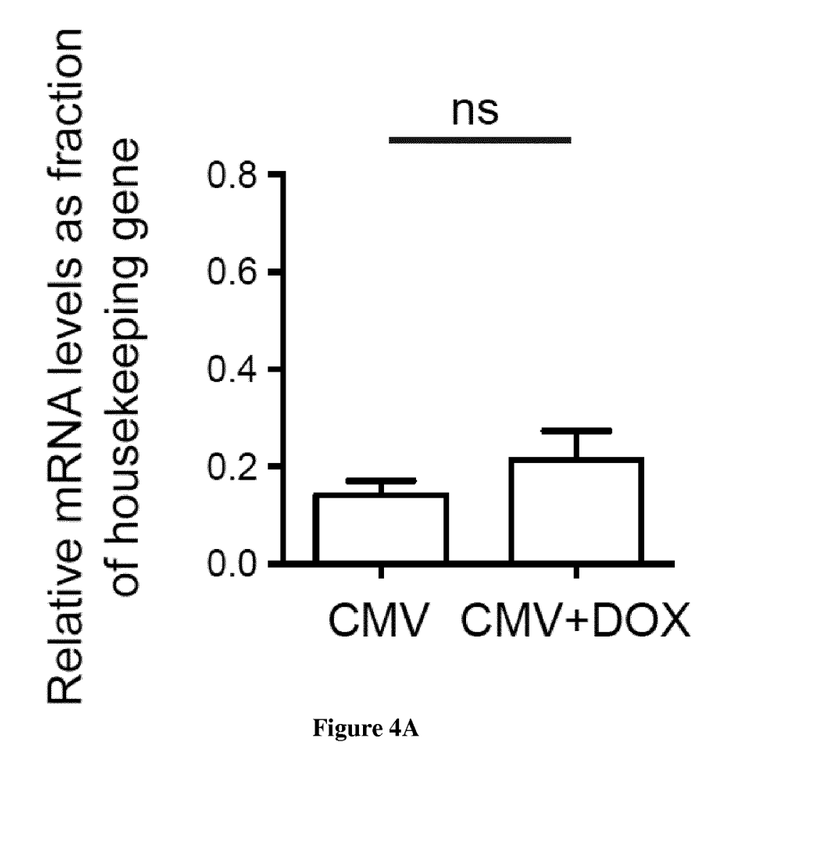
Figure 4B:
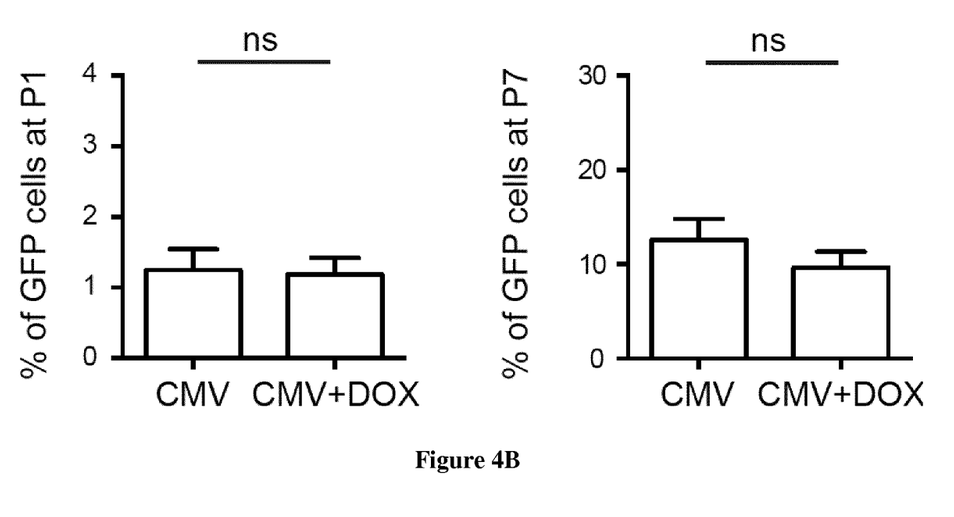

The consequences of in utero treatment with doxycycline on brain CMV infection per se were also evaluated. No significant difference in GFP gene expression was found by qRT-PCR between treated and untreated CMV-infected brains at P1 (FIG. 4A). Moreover, the proportions of CMV-infected, GFP$^+$ cells as detected by flow cytometry analysis performed on CD45$^+$ hematopoietic cells isolated from CMV-infected brains at P1, were not significantly different between doxycycline-treated and untreated pups (FIG. 4B). Also, no significant difference in GFP$^+$ infected cells was found by flow cytometry at P7 between doxycycline-treated and untreated pups. Hence the early and transient impact of doxycycline on microglia phenotype, was not accompanied by a parallel decrease in CMV infection of the brain.

Chronic Doxycycline Administration to the Mother Throughout Pregnancy Improves the Postnatal Outcome Owing to the transient improvement of microglia status upon maternal administration of doxycycline during pregnancy, we then tested whether this would in turn impact on the postnatal outcome. In doxycycline-treated, CMV-infected pups, survival rate improved significantly as compared to infected pups from untreated dams (FIG. 1A): CMV-infected pups treated with doxycycline in utero had a risk 5.1 lower to postnatal death in the first three postnatal weeks, than their untreated, CMV-infected counterparts ($p=0.0006$). At P20, 86.1% (n=31 out of 36 newborns) of infected pups from doxycycline-treated dams had survived as compared to 29.6% (n=16 out of 54 newborns) of infected pups from untreated dams ($p<0.001$, Chi2 test). Significant improvement in body weight gain was also observed in CMV-infected pups after doxycycline treatment in utero ($p<10^{-4}$; FIG. 1B).

Whereas no rescue could be obtained at P40 on hearing threshold after doxycycline treatment (data not shown), responses to sensorimotor tests (righting and cliff aversion reflexes) improved significantly ($p=0.025$ and $p<10^{-4}$, respectively) in infected pups treated with doxycycline in utero (success to righting: odds ratio 2.6; success to cliff aversion: odds ratio 9.9) (FIG. 1C, 1D). When only the subset of the rat pups who successfully performed the righting reflex were considered, no significant difference in the time to succeed was observed after doxycycline treatment ($p=0.24$), consistent with the lack of significant difference between CMV-infected pups and control (MEM-injected) pups previously found. In contrast, time to perform successfully the cliff aversion test was significantly decreased after doxycycline treatment ($p=0.0009$).

Hindlimb paralysis was also observed less frequently after doxycycline administration (FIG. 1E). Hence, 50% (n=18 out of 36) of doxycycline-treated, CMV-infected pups displayed paralysis during the first three postnatal weeks, as compared to 83.3% (n=45 out of 54) in the untreated counterparts ($p=0.001$); consistently, the risk of hindlimb paralysis dropped down by 6.2 fold ($p=0.03$). Whereas the proportion of epileptic, CMV-infected rats decreased, albeit not significantly ($p=0.12$), upon treatment with doxycycline (11%) as compared with untreated, infected rats (24%), the risk of epileptic seizures during the period of evaluation decreased significantly by 5.9 fold in CMV-infected rats who had been given doxycycline in utero ($p<10^{-4}$; FIG. 1F).

Hence, while doxycycline administration during pregnancy did not significantly modify the amount of active CMV infection of the developing brain after birth, it led to a transient modification of microglia phenotype that was associated with long-term favorable effects on survival, weight gain and neurodevelopmental outcomes.

REFERENCES

Throughout this application, various references describe the state of the art to which this invention pertains. The disclosures of these references are hereby incorporated by reference into the present disclosure.

1. Adler S P & Nigro G (2013) Prevention of maternal-fetal transmission of cytomegalovirus. Clin Infect Dis 57 Suppl 4: S189-192.
2. Cheeran M C, Lokensgard J R, & Schleiss M R (2009) Neuropathogenesis of congenital cytomegalovirus infection: disease mechanisms and prospects for intervention. Clinical microbiology reviews 22(1):99-126, Table of Contents.
3. William J. Britt DCaSJ (2013) Murine Model of Neonatal Cytomegalovirus Infection. Cytomegaloviruses: From Molecular Pathogenesis to Intervention, ed Lemmermann) MJRwtaoNAW (Caister Academic Press, Mainz), Vol 2, p 1046.
4. Cekinovic D, Lisnic V J, & Jonjic S (2014) Rodent models of congenital cytomegalovirus infection. Methods in molecular biology 1119:289-310.
5. Kosmac K, et al. (2013) Glucocorticoid treatment of MCMV infected newborn mice attenuates CNS inflammation and limits deficits in cerebellar development. PLoS Pathog 9(3):e1003200.
6. Sakao-Suzuki M, et al. (2014) Aberrant fetal macrophage/microglial reactions to cytomegalovirus infection. Annals of clinical and translational neurology 1(8):570-588.
7. Bradford R D, et al. (2015) Murine CMV-induced hearing loss is associated with inner ear inflammation and loss of spiral ganglia neurons. PLoS Pathog 11(4):e1004774.
8. Slavuljica I, et al. (2015) Immunobiology of congenital cytomegalovirus infection of the central nervous system-the murine cytomegalovirus model. Cell Mol Immunol 12(2): 180-191.
9. Cloarec R, et al. (2016) Cytomegalovirus Infection of the Rat Developing Brain In Utero Prominently Targets Immune Cells and Promotes Early Microglial Activation. PLoS One 11(7):e0160176.
10. Seleme M C, Kosmac K, Jonjic S, & Britt W J (2017) Tumor Necrosis Factor Alpha-Induced Recruitment of Inflammatory Mononuclear Cells Leads to Inflammation and Altered Brain Development in Murine Cytomegalovirus-Infected Newborn Mice. J Virol 91(8).
11. Teissier N, et al. (2014) Cytomegalovirus-induced brain malformations in fetuses. Journal of neuropathology and experimental neurology 73(2):143-158.
12. Kosugi I, Kawasaki H, Arai Y, & Tsutsui Y (2002) Innate immune responses to cytomegalovirus infection in the developing mouse brain and their evasion by virus-infected neurons. Am J Pathol 161(3):919-928.
13. Ginhoux F, et al. (2010) Fate mapping analysis reveals that adult microglia derive from primitive macrophages. Science 330(6005): 841-845.
14. Ginhoux F, Lim S, Hoeffel G, Low D, & Huber T (2013) Origin and differentiation of microglia. Front Cell Neurosci 7:45.
15. Ginhoux F & Jung S (2014) Monocytes and macrophages: developmental pathways and tissue homeostasis. Nat Rev Immunol 14(6):392-404.
16. Frost J L & Schafer D P (2016) Microglia: Architects of the Developing Nervous System. Trends Cell Biol 26(8): 587-597.

17. Baca Jones C C, et al. (2009) Rat cytomegalovirus infection depletes MHC II in bone marrow derived dendritic cells. Virology 388(1):78-90.

18. Salmi M, et al. (2013) Tubacin prevents neuronal migration defects and epileptic activity caused by rat Srpx2 silencing in utero. Brain 136(Pt 8):2457-2473.

19. Khazipov R, et al. (2015) Atlas of the Postnatal Rat Brain in Stereotaxic Coordinates. Front Neuroanat 9:161.

20. Smith R J, Bale J F, Jr., & White K R (2005) Sensorineural hearing loss in children. Lancet 365(9462):879-890.

21. Colver A, Fairhurst C, & Pharoah P O (2014) Cerebral palsy. Lancet 383(9924):1240-1249.

22. Rousset C I, et al. (2013) Maternal exposure to lipopolysaccharide leads to transient motor dysfunction in neonatal rats. Dev Neurosci 35(2-3):172-181.

23. Suzuki Y, Toribe Y, Mogami Y, Yanagihara K, & Nishikawa M (2008) Epilepsy in patients with congenital cytomegalovirus infection. Brain Dev 30(6):420-424.

24. Cunningham C L, Martinez-Cerdeno V, & Noctor S C (2013) Microglia regulate the number of neural precursor cells in the developing cerebral cortex. J Neurosci 33(10):4216-4233.

25. Tikka T, Fiebich B L, Goldsteins G, Keinanen R, & Koistinaho J (2001) Minocycline, a tetracycline derivative, is neuroprotective against excitotoxicity by inhibiting activation and proliferation of microglia. J Neurosci 21(8):2580-2588.

Thomas Skripuletz, et al. The antiviral drug ganciclovir does not inhibit microglial proliferation and activation. Scientific Reports|5:14935|DOI: 10.1038/srep14935.

Abraham Jayne et al. Minocycline attenuates microglia activation and blocks the long-term epileptogenic effects of early-life seizures. Neurobiology of Disease 46 (2012) 425-430.

Yrjanheikki Juha et al. Tetracyclines inhibit microglial activation and are neuroprotective in global brain ischemia. Proc. Natl. Acad. Sci. USA Vol. 95, pp. 15769-15774, December 1998 Neurobiology.

Cloarec R, Bauer S, Teissier N, Schaller F, Luche H, Courtens S, Salmi M, Pauly V, Bois E, Pallesi-Pocachard E, Buhler E, Michel F J, Gressens P, Malissen M, Stamminger T, Streblow D N, Bruneau N, Szepetowski P. In Utero Administration of Drugs Targeting Microglia Improves the Neurodevelopmental Outcome Following Cytomegalovirus Infection of the Rat Fetal Brain.

The invention claimed is:

1. A method of treating cytomegalovirus (CMV) related diseases in a subject in need thereof, comprising administering to the subject a therapeutically effective amount of a compound that modifies microglia, wherein the compound is clodronate or a tetracycline family compound, and wherein the CMV related disease is a disorder associated with perinatal or congenital CMV infection selected from the group consisting of microcephaly, polymicrogyria, hearing loss, cerebral palsy, epileptic seizures and intellectual disability.

2. The method according to claim 1, wherein said compound depletes and/or inhibits the microglia.

3. The method according to claim 1, wherein said compound is a tetracycline family compound.

4. The method according to claim 3 wherein the tetracycline family compound is doxycycline.

5. A method of treating or inhibiting at least one cytomegalovirus (CMV) related neurodevelopmental disorder in a foetus in need thereof, comprising administering to a pregnant female or the foetus in utero a therapeutically effective amount of a compound which reduces activity of microglia or depletes the microglia, wherein said compound is clodronate or a tetracycline family compound.

6. The method according to claim 5 wherein the tetracycline family compound is doxycycline.

7. The method of claim 5, wherein the at least one neurodevelopmental disorder is selected from the group consisting of retinitis, microcephaly, polymicrogyria, hearing loss, cerebral palsy, epileptic seizures and intellectual disability.

8. The method of claim 5, wherein the at least one neurodevelopmental disorder is selected from the group consisting of microcephaly, polymicrogyria, hearing loss, cerebral palsy, epileptic seizures and intellectual disability.

9. A method of treating or inhibiting at least one cytomegalovirus (CMV) related neurodevelopmental disorder in a newborn baby in need thereof, comprising administering to the newborn baby a therapeutically effective amount of a compound which reduces activity of microglia or depletes the microglia, wherein said compound is clodronate or a tetracycline family compound.

10. The method according to claim 9 wherein the tetracycline family compound is doxycycline.

11. The method of claim 9, wherein the at least one neurodevelopmental disorder is selected from the group consisting of retinitis, microcephaly, polymicrogyria, hearing loss, cerebral palsy, epileptic seizures and intellectual disability.

12. The method of claim 9, wherein the at least one neurodevelopmental disorder is selected from the group consisting of microcephaly, polymicrogyria, hearing loss, cerebral palsy, epileptic seizures and intellectual disability.

* * * * *